April 23, 1968 M. A. LOGAN Plant Pat. 2,808
PEACH TREE
Filed Dec. 16, 1966
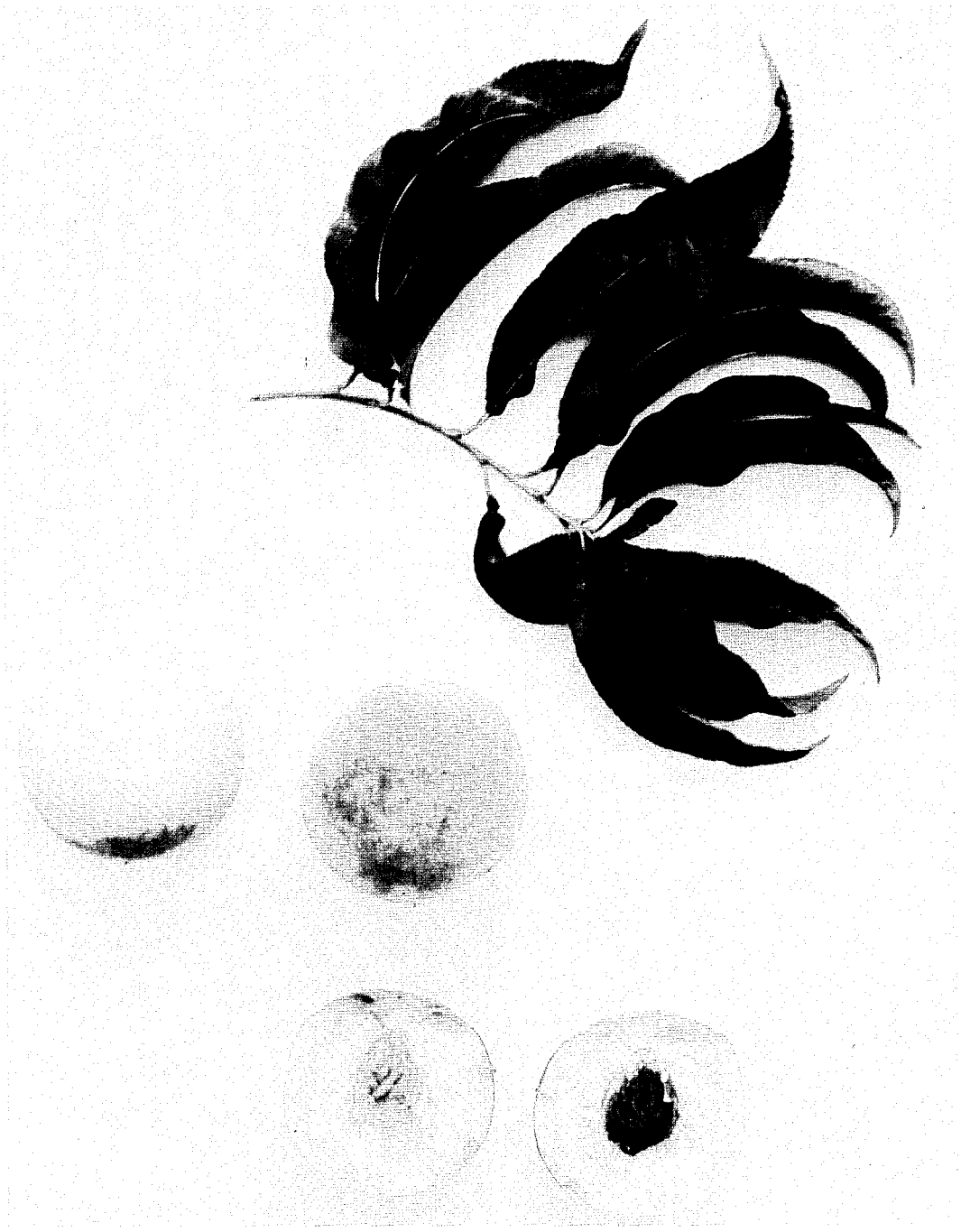
INVENTOR
Mabel A. Logan
BY
Webster & Webster
ATTORNEYS United States Patent Office Plant Pat. 2,808
Patented Apr. 23, 1968

2,808
PEACH TREE

Mabel A. Logan, Rte. 2, Box 1269,
Grass Valley, Calif. 95945

Filed Dec. 16, 1966, Ser. No. 602,431
1 Claim. (Cl. Plt.—42)

This discovery relates to a new and distinct variety of peach tree which is a regular and very productive bearer of large, globose, freestone fruit having white flesh streaked and flecked with red, and light yellow skin overspread to a substantial extent with red which is partially streaked and mottled.

The fruit of the present variety provides an excellent, late mid-season white-fleshed peach of good eating quality and a delicious flavor; a characteristic feature being a ripening period of the fruit about four to five weeks later than the Nectar (unpatented) and which the present variety somewhat resembles.

The herein claimed variety of peach tree was discovered by me growing as a chance seedling in the yard of my residence located in the Cedar Ridge area near Grass Valley, Nevada County, Calif. When such chance seedling, which was maintained under care, began to bear fruit I recognized—upon close and continuing observation—that such seedling was quite different in comparison to another peach varieties, both in the character and quality of the fruit and the ripening period.

Subsequent to recognition by me that the variety was novel and distinct, such variety was asexually reproduced—upon my order and on my behalf—by a commercial nursery at its Mt. Pleasant growing grounds located near Lincoln, Placer County, Calif.; such asexual reproduction having been accomplished by budding onto Lovell (unpatented) roostock. All of such asexual reproductions were found to run true to the original tree in all respects.

The drawing is an illustration, by photographic reproduction in color, of a twig with leaves, two whole fruit, and another fruit cut in half to expose the flesh and with the stone remaining in one half.

Referring now more specifically to the pomological details of this new and distinct variety of peach tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Upright.
- *Density.*—Open.
- *Form.*—Vase-formed.
- *Hardiness.*—Half hardy.
- *Production.*—Very productive.
- *Bearing.*—Regular bearer.

Trunk:
- *Size.*—Slender.
- *Texture.*—Medium.

Branches:
- *Size.*—Slender.
- *Texture.*—Medium.
- *Color.*—Dull brown.
- *Lenticels.*—Number—numerous. Size—medium.

Leaves:
- *Size.*—Large. Average length—5½". Average width—1½".
- *Form.*—Lanceolate; acutely pointed.
- *Thickness.*—Medium.
- *Texture.*—Smooth.

- *Margin.*—Glandular; finely serrate.
- *Petiole.*—Length—medium, average ½". Thickness—medium.
- *Glands.*—Average number—2. Opposite; medium size; reniform; green; positioned on petiole adjacent base of blade.
- *Stipules.*—Present.
- *Color.*—Top side—medium green (23–L–8). Under side—lighter green (22–L–6).

Flower buds:
- *Hardiness.*—Half hardy.
- *Size.*—Medium.
- *Length.*—Medium.
- *Form.*—Pointed; free.

Flowers:
- *Blooming period.*—Date of first bloom—Mar. 3, 1966. Date of full bloom—Mar. 13, 1966. Medium, as compared with other varieties.
- *Size.*—Medium.
- *Color.*—Pink.

Fruit:
- *Maturity when described.*—Eating ripe—third week in August.
- *Date of first picking.*—Aug. 21, 1966.
- *Date of last picking.*—Aug. 28, 1966.
- *Size.*—Uniform—large. Average diameter axially—2¾". Average transversely in suture plane—2½".
- *Form.*—Uniform; symmetrical. Globose—oblong.
- *Suture.*—Shallow, with marked depression beyond pistil point.
- *Ventral surface.*—Rounded slightly; lipped toward both sides.
- *Lips.*—Equal.
- *Cavity.*—Circular; elongated in suture plane with suture showing on one side. Average depth—⅜". Average breadth—⅜".
- *Base.*—Rounded.
- *Apex.*—Rounded.
- *Pistil point.*—Oblique.

Skin:
- *Thickness.*—Medium.
- *Texture.*—Medium.
- *Tendency to crack.*—None.
- *Down.*—Moderate.
- *Color.*—Light yellow (9–H–1) overspread to a substantial extent with red (4–L–7—6–L–7); the red being partially streaked and mottled.

Flesh:
- *Amygdalin.*—Scant.
- *Texture.*—Medium.
- *Fibers.*—Few; fine.
- *Ripens.*—Evenly.
- *Flavor.*—Subacid.
- *Aroma.*—Distinct.
- *Eating quality.*—Best.
- *Color.*—White (9–D–1) with slight yellow tinge; the flesh being streaked and flecked with red (4–K–5). Surface of pit cavity—red (4–K–5), with white fibers.

Stone:
- *Type.*—Free; parts from flesh smoothly.
- *Size.*—Medium. Average length—⅞". Average breadth—½". Average thickness—⅜".
- *Fibers.*—Short.
- *Form.*—Globose.
- *Hilum.*—Narrow.
- *Apex.*—Rounded.
- *Sides.*—Equal.
- *Surface.*—Regularly furrowed toward apex; ridged throughout.
- *Ridges.*—Rounded; continuous.
- *Pits.*—Circular.

*Ventral edge.*—Thin, with wing throughout.

*Dorsal edge.*—Narrow, with narrow groove.

*Tendency of split.*—Slight.

*Color.*—Ruby red (7–H–6) when freshly removed.

Use: Market—Local. Dessert.

Keeping quality: Good.

Shipping quality: Good.

The tree and its fruit herein described may vary in slight detail due to climatic and soil conditions under which the variety may be grown; the present description being of the variety as grown in the foothill region of northern California.

The following is claimed:

1. A new and distinct variety of peach tree, substantially as illustrated and described, characterized by the regular and productive bearing of large, globose, freestone fruit having white flesh streaked and flecked with red, and a light yellow skin overspread to a substantial extent with red which is partially streaked and mottled; and further characterized, in comparison to the nectar which it generally resembles, by fruit having a ripening period four to five weeks later.

No references cited.

ROBERT E. BAGWILL, *Primary Examiner.*